US010267729B2

(12) United States Patent
Jones et al.

(10) Patent No.: US 10,267,729 B2
(45) Date of Patent: Apr. 23, 2019

(54) SYSTEMS AND METHODS FOR DETECTING GAS LEAKS

(71) Applicant: Kairos Aerospace Inc., Los Altos, CA (US)

(72) Inventors: Brian Butler Jones, Los Altos, CA (US); Steven William Deiker, Los Altos Hills, CA (US)

(73) Assignee: KAIROS AEROSPACE INC., Los Altos, CA (US)

( * ) Notice: Subject to any disclaimer, the term of this patent is extended or adjusted under 35 U.S.C. 154(b) by 0 days.

(21) Appl. No.: 14/707,556

(22) Filed: May 8, 2015

(65) Prior Publication Data
US 2015/0323449 A1 Nov. 12, 2015

Related U.S. Application Data

(60) Provisional application No. 61/991,012, filed on May 9, 2014.

(51) Int. Cl.
G01N 21/00 (2006.01)
G01M 3/00 (2006.01)
(Continued)

(52) U.S. Cl.
CPC ........ G01N 21/3504 (2013.01); G01M 3/205 (2013.01); G01M 3/38 (2013.01);
(Continued)

(58) Field of Classification Search
USPC ................................................ 356/432–444
See application file for complete search history.

(56) References Cited

U.S. PATENT DOCUMENTS 3,788,742 A * 1/1974 Garbuny ................ G01N 21/39
356/218
3,829,694 A * 8/1974 Goto .................. G01N 21/3504
250/338.5
(Continued)

FOREIGN PATENT DOCUMENTS

EP 2264433 A1 12/2010

OTHER PUBLICATIONS

International Search Report and Written Opinion issued by the U.S. Patent and Trademark Office as Searching Authority in PCT/US15/29943, dated Aug. 5, 2015 (9 pages).

Primary Examiner — Shawn Decenzo
Assistant Examiner — Jarreas C Underwood
(74) Attorney, Agent, or Firm — Goodwin Procter LLP

(57) ABSTRACT

The invention is directed to improved systems, methods, and computer readable media for detecting gas leaks. More particularly, the invention detects gas leaks or discharges, such as methane or any other suitable gases, by analyzing reflected or direct light that passes through a region of enhanced target gas concentration. The invention collects light and processes spectral data of the light. All molecules are subject to rotational motions, vibrational motions, and/or combinations thereof (rovibrational motions), in which the atoms in the molecule are vibrating with respect to each other and/or rotating around each other. When the light passes through the region of the target gas, a portion of the light with certain wavelengths will be absorbed by the target gas due to the rovibrational motions of the target gas molecules. By analyzing the magnitude of absorption at certain wavelengths, one can determine the concentration of certain target gas or gases.

20 Claims, 11 Drawing Sheets

(51) Int. Cl.
  *G01N 21/3504* (2014.01)
  *G01N 21/31* (2006.01)
  *G01N 21/90* (2006.01)
  *G01M 3/20* (2006.01)
  *G01M 3/38* (2006.01)
  *G01N 21/17* (2006.01)

(52) U.S. Cl.
  CPC ......... *G01N 21/3103* (2013.01); *G01N 21/90* (2013.01); *G01N 2021/1795* (2013.01); *G01N 2021/3531* (2013.01)

(56) References Cited

U.S. PATENT DOCUMENTS

| | | | | |
|---|---|---|---|---|
| 3,843,258 A * | 10/1974 | Shupe | ............... | G01N 21/314 250/338.5 |
| 3,995,960 A * | 12/1976 | Fletcher | ............. | G01N 21/1702 250/343 |
| 4,425,503 A * | 1/1984 | Watkins | ................ | G01N 21/39 250/338.5 |
| 4,489,239 A * | 12/1984 | Grant | ..................... | G01N 21/39 250/338.5 |
| 4,555,627 A * | 11/1985 | McRae, Jr. | ............. | G01M 3/38 250/330 |
| 4,810,884 A * | 3/1989 | Carlson | ................ | G01N 21/72 250/338.5 |
| 5,015,099 A * | 5/1991 | Nagai | .................... | G01N 21/39 250/338.5 |
| 5,026,991 A * | 6/1991 | Goldstein | ............. | G01N 21/39 250/339.04 |
| 5,166,789 A * | 11/1992 | Myrick | ................... | G01V 9/00 348/144 |
| 5,294,796 A * | 3/1994 | Fee | ........................ | G01N 21/39 250/338.5 |
| 5,298,751 A * | 3/1994 | Fee | .................... | G01N 21/3518 250/338.5 |
| 5,317,156 A * | 5/1994 | Cooper | ................. | G01N 21/39 250/339.13 |
| 5,373,160 A * | 12/1994 | Taylor | .................... | G01N 21/39 250/338.5 |
| 5,430,293 A * | 7/1995 | Sato | ........................ | G01M 3/38 250/330 |
| 5,608,520 A * | 3/1997 | Fleming | ............... | G01N 21/718 356/318 |
| 5,656,813 A * | 8/1997 | Moore | ............... | G01N 21/3504 250/330 |
| 6,211,796 B1 * | 4/2001 | Toms | ................... | A47B 83/001 307/147 |
| 6,789,021 B2 * | 9/2004 | Rendahl | .............. | G01M 15/102 702/130 |
| 6,853,452 B1 * | 2/2005 | Laufer | ............... | G01N 21/3504 356/436 |
| 6,885,965 B2 * | 4/2005 | Butler | ....................... | G01J 3/28 356/451 |
| 6,995,846 B2 * | 2/2006 | Kalayeh | .................. | G01N 21/31 250/338.5 |
| 7,501,629 B2 * | 3/2009 | Hashmonay | ....... | G01N 21/3504 250/339.08 |
| 7,606,437 B2 * | 10/2009 | Gallagher | ......... | G06F 17/30265 382/254 |
| 7,710,568 B1 * | 5/2010 | Paige | .................... | G01J 3/0264 356/328 |
| 7,755,041 B2 * | 7/2010 | Killinger | ............ | G01N 21/3504 250/300 |
| 8,269,171 B2 * | 9/2012 | Gorin | ................. | G01N 21/3504 250/338.5 |
| 8,269,971 B1 * | 9/2012 | Marsh | ................ | G01N 21/3504 356/432 |
| 8,803,093 B2 * | 8/2014 | Jonsson | ............ | G01N 21/3518 250/339.01 |
| 8,823,938 B2 * | 9/2014 | Beck | .................... | G01N 21/314 356/432 |
| 9,166,358 B2 * | 10/2015 | Miles | .................. | G01N 21/1717 |
| 9,258,535 B2 * | 2/2016 | Pool | ..................... | H04N 5/2256 |
| 9,438,865 B2 * | 9/2016 | Renkis | .................. | H04N 7/181 |
| 10,033,910 B2 * | 7/2018 | Lenigk | ....................... | H04N 5/04 |
| 2005/0134859 A1 | 6/2005 | Kalayeh et al. | | |
| 2008/0092625 A1 * | 4/2008 | Hinnrichs | ................. | G01J 3/02 73/23.2 |
| 2010/0097396 A1 * | 4/2010 | Lee | ................ | H04N 21/234327 345/629 |

* cited by examiner

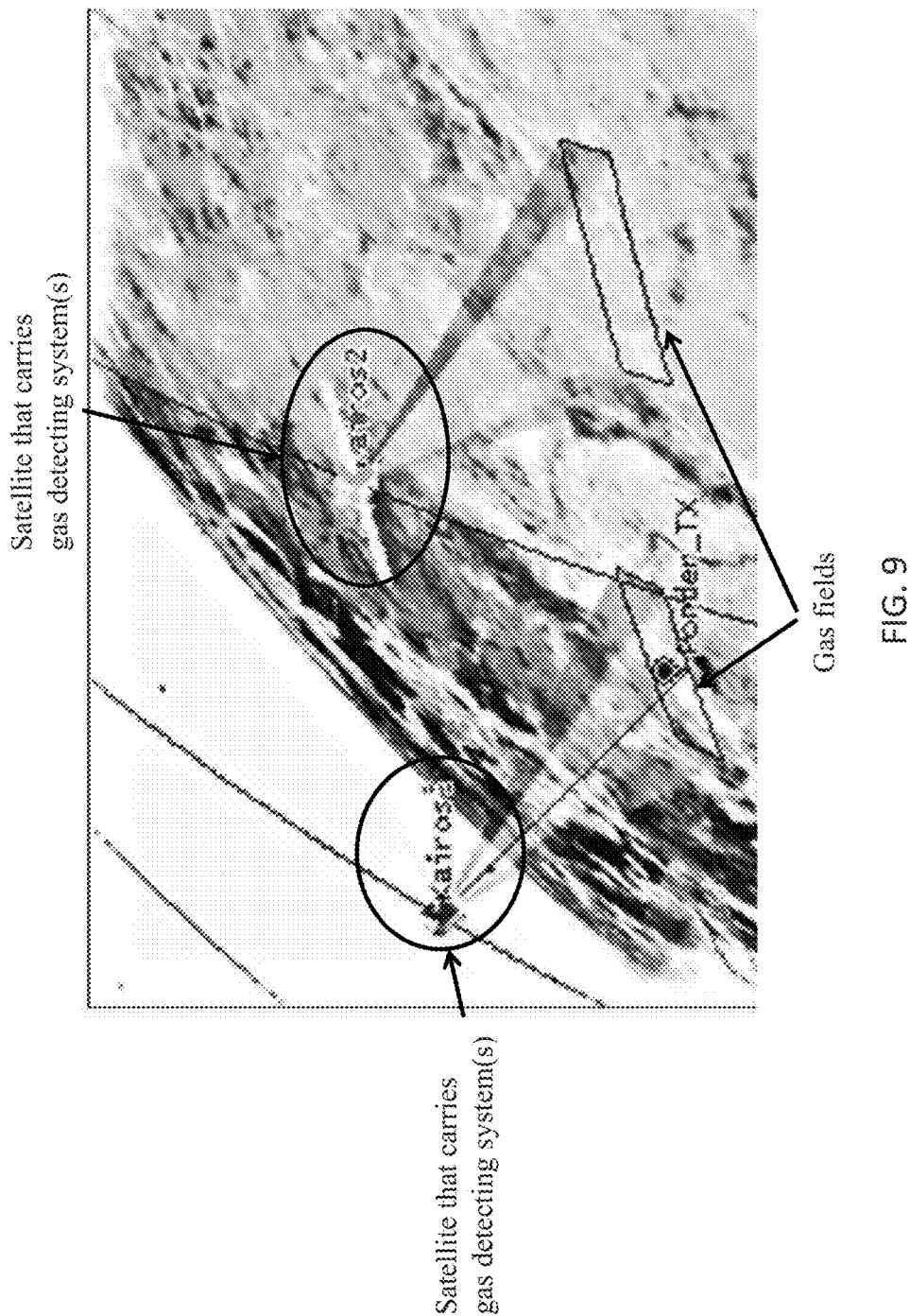

SYSTEMS AND METHODS FOR DETECTING GAS LEAKS

RELATED APPLICATION

This application claims priority to U.S. Provisional Patent Application No. 61/991,012, titled "Systems And Methods For Detecting Gas Leaks," which was filed on May 9, 2014 and is incorporated herein in its entirety.

BACKGROUND OF THE INVENTION

Technical Field

The invention relates generally to the field of systems and methods for detecting gas leaks.

Description of the Related Art

The leakage of natural gas from wells, associated equipment, pipelines, distribution networks, and other points leads to a loss of between approximately 1.5% to 8% or more of the total natural gas extracted from the ground. Additionally, the leakage may have a significant safety and environmental impact. Therefore, there is a need for governments, organizations, and natural gas companies to periodically inspect potential leak sites and detect any leakage.

Traditionally, fugitive emission detection in gas fields is done primarily with forward-looking infrared cameras (FLIRs). This camera provides video imagery that is sensitive to the temperature differences between the leaking natural gas and the surrounding atmosphere. This camera is typically hand-held and shows a real-time screen much like a consumer digital camera. The result is entirely qualitative and relies on the observation and judgment of a human operator. For example, methane leaks appear as a smoke-like vapor emitting from the leak site.

In cases where a more quantitative measurement is desired, measurements are taken according to the Environmental Protection Agency's Method 21—Determination of Volatile Organic Compound Leaks. Method 21 is an official standard by which leaks can be quantitatively measured and shown to be in or out of compliance with any regulation. Method 21 provides the requisite calibration accuracy, response time, and sensitivity for any device intended to provide regulatory compliance measurements. Typically, Method 21 instrumentation records the concentration of various volatile organic compounds by using a probe with a single-end opening to directly sample the air in proximity to a leak site.

These known leak detection systems and methods suffer from a number of drawbacks and deficiencies. First, they are labor intensive and costly. Each potential leak site must be physically visited by at least one test technician. The technician must then systematically examine the entire surface of the site with the leak detection device. Depending on the size of the site in question, this can require from an hour to several hours or days of the technician's labor. With many organizations having hundreds or thousands of sites to examine, many technicians and leak detection devices are required in order to perform periodic (e.g., monthly) inspections of every site. However, because of this high cost, most sites are currently not inspected on a periodic basis. Nevertheless, new regulations may require a higher frequency of inspection, which may represent a significant monetary burden in testing.

Second, these systems and methods are subject to variation in a technician's experience and performance, and also to the technician's error. Different technicians may apply different levels of thoroughness in the inspection of the site, leading to different outcomes.

Third, these solutions are not scalable. As the number of sites and the visiting frequency per site increases, the number of technicians and leak detection devices required also increases proportionally. The result is that the cost of monitoring gas leakage via these systems and methods grows rapidly.

Therefore, there is a need in the art to provide systems and methods for improving the detection of gas leaks. Accordingly, it is desirable to provide methods and systems that overcome these and other deficiencies of the related art.

SUMMARY

In accordance with the disclosed subject matter, systems, methods, and computer readable media are provided for detecting gas leaks.

Disclosed subject matter includes, in one aspect, an apparatus for detecting gas leaks. The apparatus includes an optical component configured to collect light. The apparatus includes a spectrometer configured to receive and process the light to generate raw spectral data. The apparatus includes a memory that stores a module. The apparatus includes a processor configured to run the module stored in the memory that is configured to cause the processor to: receive the raw spectral data; generate preprocessed spectral data by subtracting noise from the raw spectral data; identify a first wavelength range that is sensitive to a target gas and a second wavelength range that is not sensitive to the target gas; process the preprocessed spectral data in the first wavelength range to generate an absorption power level; process the preprocessed spectral data in the second wavelength range to generate a reference power level; and compare the absorption power level to the reference power level to determine a concentration of the target gas.

Disclosed subject matter includes, in another aspect, a method for detecting gas leaks. The method includes collecting light. The method includes processing the light to generate raw spectral data. The method includes generating preprocessed spectral data by subtracting noise from the raw spectral data. The method includes identifying a first wavelength range that is sensitive to a target gas and a second wavelength range that is not sensitive to the target gas. The method includes processing the preprocessed spectral data in the first wavelength range to generate an absorption power level. The method includes processing the preprocessed spectral data in the second wavelength range to generate a reference power level. The method includes comparing the absorption power level to the reference power level to determine a concentration of the target gas.

Disclosed subject matter includes, in yet another aspect, a computer readable medium for detecting gas leaks. The non-transitory computer readable medium can include executable instructions operable to cause an apparatus to collect light. The instructions are further operable to process the light to generate raw spectral data. The instructions are further operable to generate preprocessed spectral data by subtracting noise from the raw spectral data. The instructions are further operable to identify a first wavelength range that is sensitive to a target gas and a second wavelength range that is not sensitive to the target gas. The instructions are further operable to process the preprocessed spectral data in the first wavelength range to generate an absorption power level. The instructions are further operable to process the preprocessed spectral data in the second wavelength range to generate a reference power level. The instructions are further operable to compare the absorption power level to the reference power level to determine a concentration of the target gas.

There has thus been outlined, rather broadly, the features of the disclosed subject matter in order that the detailed description thereof that follows may be better understood, and in order that the present contribution to the art may be better appreciated. There are, of course, additional features of the disclosed subject matter that will be described hereinafter and which will form the subject matter of the claims appended hereto.

In this respect, before explaining at least one embodiment of the disclosed subject matter in detail, it is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the disclosed subject matter. It is important, therefore, that the claims be regarded as including such equivalent constructions insofar as they do not depart from the spirit and scope of the disclosed subject matter.

These together with the other objects of the disclosed subject matter, along with the various features of novelty which characterize the disclosed subject matter, are pointed out with particularity in the claims annexed to and forming a part of this disclosure. For a better understanding of the disclosed subject matter, its operating advantages and the specific objects attained by its uses, reference should be made to the accompanying drawings and descriptive matter in which there are illustrated preferred embodiments of the disclosed subject matter.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 9 illustrates an exemplar embodiment where the gas detector system is mounted on one or more satellites.

DETAILED DESCRIPTION

In the following description, numerous specific details are set forth regarding the systems, methods and media of the disclosed subject matter and the environment in which such systems, methods and media may operate, etc., in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the examples provided below are exemplary, and that it is contemplated that there are other systems, methods and media that are within the scope of the disclosed subject matter.

The invention is directed to improved systems and methods for detecting gas leaks. More particularly, the invention detects gas leaks or discharges, such as methane or any other suitable gases, by analyzing reflected or direct sunlight, or light in general, that passes through a region of enhanced target gas concentration. All molecules are subject to rotational motions, vibrational motions, and/or combinations thereof (rovibrational motions), in which the atoms in the molecule are vibrating with respect to each other and/or rotating around each other. The frequencies of these rotational, vibrational, and rovibrational motions are determined by the laws of quantum mechanics, and typically can only exist at certain discrete values. When the light passes through the region of the enhanced gas concentration, gas molecules in the region will absorb certain portions of the light that have the frequencies at or near to the frequencies of the rotational, vibrational, and rovibrational motions of the gas molecules. Because for the light or any electromagnetic waves in general, its frequency and wavelength are inversely related, it is equivalent to say when the light passes thought the region of the enhanced gas concentration, certain wavelengths of the light would be absorbed by the gas molecules in the region. By analyzing the magnitude of absorption at certain wavelength or wavelengths, one can determine the concentration of certain target gas or gases.

Figure 1A:
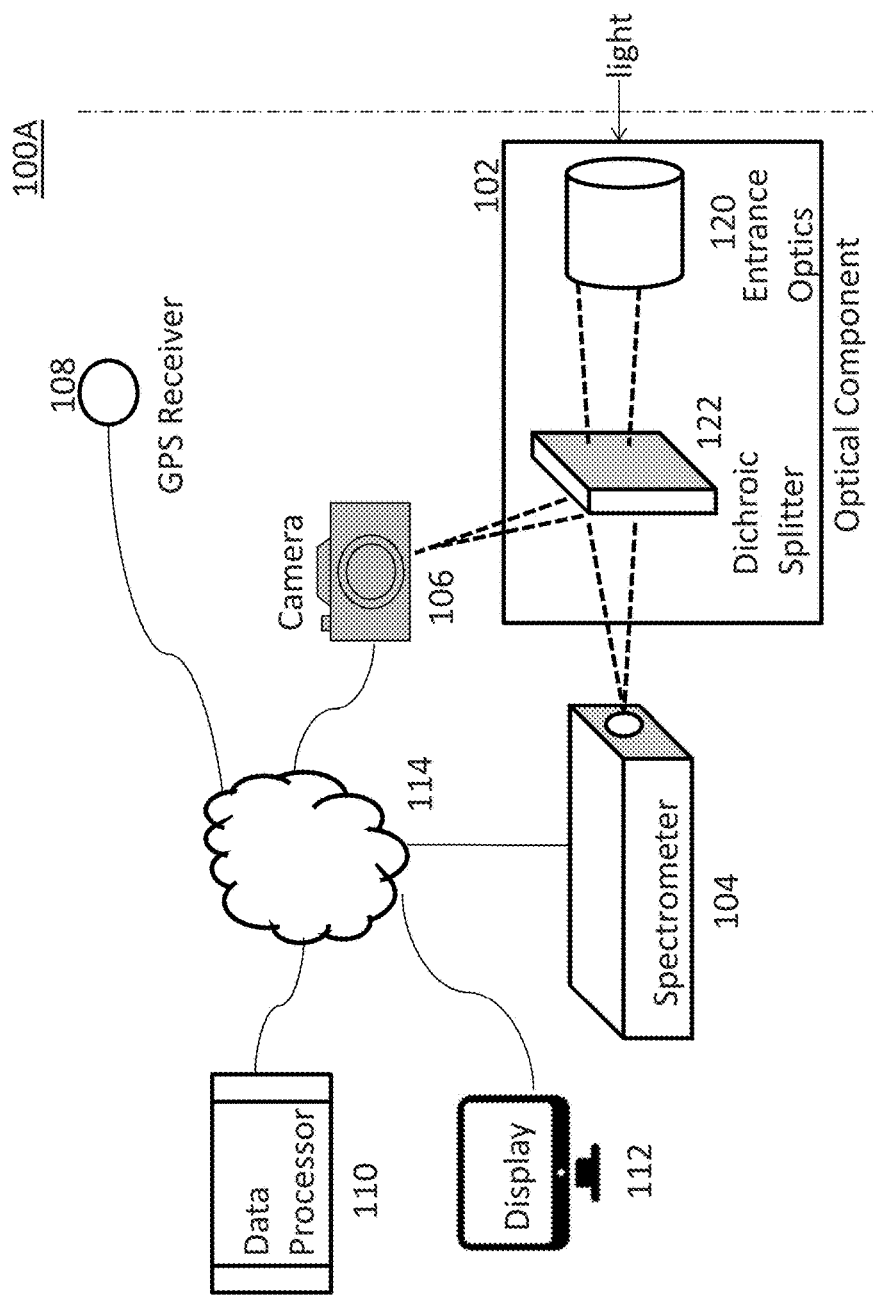
FIGS. 1(a), 1(b), and 1(c) illustrate three gas detector systems in accordance with certain embodiments of the disclosed subject matter.

FIG. 1(a) illustrates an exemplary gas detector system 100A in accordance with an embodiment of the disclosed subject matter. The system 100A described here is configured to detect gas leaks or discharges, such as methane or any other suitable gas or gases, by analyzing reflected or direct light that passes through a region of enhanced gas concentration. The system 100A comprises an optical component 102, a spectrometer 104, a camera 106, a GPS receiver 108, a data processor 110, a display 112, and a network 114. The components described in the system 100A can be further broken down into more than one component and/or combined together in any suitable arrangement. Further, one or more components can be rearranged, changed, added, and/or removed. For example, in some embodiments, the system 100A may also include a local storage medium and/or a remote storage medium.

The optical component 102 collects and feeds the light to the spectrometer 104 and the camera 106. In some embodiments, the optical component 102 comprises two elements:

an entrance optics 120 coupled to a dichroic splitter 122. The entrance optics collects, collimates, and condenses the light appropriately to match the requirements of the spectrometer 104 and/or the camera 106. The entrance optics 120 can collect visible wavelengths of the light, infrared wavelengths of the light, or both. The entrance optics 120 preferably has a high etendue to maximize the signal-to-noise ratio of the resulting data. Etendue is a measure of optical throughput. An optical device with high etendue delivers more light from the external light source to a focal plane than an optical device with low etendue.

The dichroic splitter 122 is an optical element that transmits some wavelengths of light and reflects other wavelengths of light. In some embodiments, the dichroic splitter 122 splits the light into at least two paths by wavelength. In some embodiments, the dichroic splitter 122 can split the light into an infrared light portion and a visible light portion. In some embodiments, the infrared light portion also includes a near-infrared light portion. In some embodiments, the infrared portion of the light is directed to the spectrometer 104 either directly or by means of a set of relay or re-imaging optics. In some embodiments, the visible portion of the light is directed to the camera 106, either directly or by means of a set of relay or re-imaging optics. The two paths may be further reflected by mirrors to form a more compact system, or to achieve other focusing or optical properties in order to optimize the performance of the instrument. In some embodiments, the spectrometer 104 can receive other portions of light in addition to the infrared light. In some embodiments, the camera 106 can receive other portions of light in addition to the visible light. In some embodiments, the output of the optical component 102 can be sent to the display 112 for display.

The spectrometer 104 receives the light from the optical component 102 and generates raw spectral data by recording the absorption of certain wavelengths of the light by the gas molecule in the region that is passed through by the light. The raw spectral data generated by the spectrometer 104 can be sent, directly or indirectly via the network 114, to the data processor 110 for processing and storage. In some embodiments, the raw spectral data generated by the spectrometer 104 can be sent to the display 112 for display. For most small molecules, the wavelengths absorbed by rovibrational motions lie in the infrared region, which can also include the near-infrared region, of the light spectrum. As a non-limiting example, the rovibrational motions of methane strongly absorb light in a range approximately between 1.650823 micrometers and 1.651396 micrometers in wavelength. In other words, when the light passes through a region of enhanced concentration of methane, the portion of the light with wavelengths approximately between 1.650823 micrometers and 1.651396 micrometers will be strongly absorbed. The range of wavelength approximately between 1.650823 micrometers and 1.651396 micrometers is also referred to as one of the absorption lines (or absorption ranges) of methane. Methane has several absorption lines, including some absorption lines between 1.6 micrometers and 1.7 micrometers in wavelength. Because methane, like any other molecule, only strongly absorbs light with certain discrete ranges of wavelengths, the light with ranges of wavelengths that are adjacent to absorption lines (e.g., the range of wavelength approximately between 1.650823 micrometers and 1.651396 micrometers), such as approximately between 1.646527 micrometers and 1.647387 micrometers, are not strongly absorbed by methane. The range of wavelength that is adjacent to an absorption line but is not strongly absorbed by methane is also referred to as one of the reference ranges of methane. There are generally at least one reference range for each absorption line. Therefore, there are several reference ranges of methane between 1.6 micrometers and 1.7 micrometers in wavelength. As non-limiting examples, Table I below lists several approximate wavelength ranges of absorption lines and reference ranges of methane.

TABLE I

| Wavelength Ranges of Absorption Line (micrometers) | Wavelength Ranges of Reference Range (micrometers) |
| --- | --- |
| 1.609949 to 1.610796 | 1.612210 to 1.613627 |
| 1.640216 to 1.640790 | 1.641364 to 1.641938 |
| 1.642798 to 1.643372 | 1.643659 to 1.644520 |
| 1.645380 to 1.645953 | 1.646527 to 1.647387 |
| 1.648246 to 1.648819 | 1.649678 to 1.650537 |
| 1.650823 to 1.651396 | 1.651682 to 1.652826 |
| 1.653683 to 1.654254 | 1.654540 to 1.655682 |
| 1.665630 to 1.666478 | 1.662797 to 1.663931 |

Other wavelengths of light may be monitored in a similar manner, either instead of or in addition to the ranges of wavelengths listed above. Further, other gases may be detected in the similar manner, via a suitable selection of wavelengths from publicly available tables of absorption lines, such as the High-resolution Transmission Molecular Absorption database ("HITRAN" or "HITRAN database"), which is a standard compilation of spectroscopic parameters used to predict the transmission of light through the atmosphere.

The spectrometer 104 preferably has a high spectral resolution (typically around 0.5 nm or better/finer) and high etendue to maximize the signal-to-noise ratio of the resulting data. Various kinds of grating and/or Fourier-transform spectrometers are appropriate, and may be selected for the system based on cost, weight, availability, or any other suitable parameters or combinations of parameters. Grating spectrometers may be of any optic design typical of grating spectrometers, including, without limitation, Czerny-Turner, Littrow, bulk grating, first-order, fiber optic, or any other suitable spectrometer, and may be based on either physically-etched or holographic gratings.

In some embodiments, the spectrometer 104 can be an imaging spectrometer. An imaging spectrometer typically uses a two-dimensional sensor plane to record spectral data in one dimension and spatial information in another dimension. Multiple exposures combined with suitable post-processing allow the creation of a two-dimensional image with spectral data embedded as a third dimension. The imaging spectrometer can be used to build up an image of the ground, where the spectral data in each pixel is used to determine leakage in that spatial area. This can be used, for example, to pinpoint the source of a gas leak within the pixel resolution, so that the cost of determining a ground leak source is minimized.

In some embodiments, the spectrometer 104 can be a hyperspectral imager. The hyperspectral imager provides spectral data in a one-dimensional push broom configuration. The hyperspectral imager is moved over the area of interest with the push broom in the cross-track direction, sweeping out a two-dimensional area on the ground. The hyperspectral imager is read out at a rate that determines the effective pixel size or resolution in the in-track direction. The pixel size is optimized between spatial resolution and signal-to-noise ratio. In one embodiment, the effective pixel size or resolution is chosen to be 30 meters (or any other suitable size), with an exposure time of about one millisecond. In some embodiments, the exposure time can be 80 milliseconds or any other suitable time. As an example, the hyperspectral imaging spectrometer could be built with a 512×640-pixel Indium Gallium Arsenide (InGaAs) detector that is optimized for response at a range centered on or substantially around 1.65. In some embodiments, the InGaAs detector can be optimized for response at other ranges, including, without limitation, between 1.6 micrometers and 1.7 micrometers. In some embodiments, other types of InGaAs detector or other types of detectors can also be used. The resulting data file would provide a spectrum observed at each 30 m by 30 m pixel on the ground. In some embodiments, other pixel sizes can also be provided. Each pixel would be evaluated independently to determine a measurement of the methane concentration as described above.

The camera 106 receives and processes the visible portion of the light that is sent by the optical component 102. The camera 106 can provide a plurality of images that correspond to the visible light. In some embodiments, the camera 106 can receive and process other portions of the light and provide a plurality of images that correspond to the portions of the light received. The camera 106 can be a digital camera, electrical camera, optical camera, or any suitable camera that can receive and process light. In some embodiments, the camera 106 collects light directly with a built-in entrance optics. When the camera 106 and the spectrometer 104 do not use the exactly same entrance optics, the spectrometer 104 and the camera 106 can be co-registered with a laboratory calibration to make sure that the camera 106 and the spectrometer 104 are pointing the same direction, so that the spectral data generated by the spectrometer 104 may be mapped to visible images generated by the camera 106 easily. In some embodiments, the images from the camera 106 can be sent, directly or indirectly via the network 114, to the data processor 110 for processing. In some embodiment, the images from the camera 106 can be sent to the display 112 for display.

In some embodiments, the system 100A can also include the GPS receiver 108. The GPS receiver 108 records location stamps of the system 100A when the sampling of light occurs by receiving location information from one or more satellites. The location stamps generated by the GPS receiver 108 and the images generated by the camera 106 can be combined to enable identification of the site from which any leaks are detected. In some embodiments, the GPS receiver 108 can additionally or alternatively provide time stamps. In some embodiments, the times stamps can be in some master clock formats, such as the Coordinated Universal Time or other suitable format. The time stamps and/or location stamps can be used to tag or match the raw spectral data generated by the spectrometer 104 and the images generated by the camera 106. In some embodiments, the location time stamps and/or time stamps can be sent, directly or indirectly via the network 114, to the data processor 110 for processing. In some embodiments, the systems 100A, 100B, and/or 100C (the systems 100B and 100C are described in connection with FIG. 1(b) and FIG. 1(c), respectively) can include one or more attitude determination sensors that can be configured to measure and/or determine the orientation of one or more components of the systems 100A, 100B, and/or 100C (the systems 100A, 100B, 100C, and/or other equivalent embodiments are collectively referred to herein as system 100). In some embodiments, the system 100 can include additional device or devices to control the attitude (e.g., the roll, pitch, and yaw) of the system 100. In some embodiments, the attitude control can be handled by any suitable existing components of the system 100.

The data processor 110 receives and processes the raw spectral data from the spectrometer 104. In some embodiments, the data processor 110 also receives outputs from the camera 106 and/or the GPS receiver 108. The structures, functions, and features of the data processor 110 are described in more detail below.

The display 112 may display one or more data from the optical component 102, the spectrometer 104, the camera 106, the GPS receiver 108, the data processor 110, and other external sources such as the Internet. The display 112 can be a dedicated terminal, a monitor on a computer or other display screen, or a web-based interface that can be accessed via a browser with typical access controls. In some embodiments, the display 112 may be physically located in proximity to the other components of the system 100A, so that an operator can observe and/or verify the output data, re-orient the system 100A, or re-acquire light in real-time or near real-time. In some embodiments, the display 112 may be physically located on the ground or at other locations that are not in proximity to other components of the system 100A, so that it may be easier for an operator to monitor, process, or analyze any results displayed by the display 112.

The components of the system 100A can be coupled, directly or indirectly, with each other via the network 114. The network 114 can include a Universal Serial Bus (USB), Ethernet, other wired connection, any wireless connection, the Internet, a cellular network, a telephone network, a computer network, a packet switching network, a line switching network, a local area network (LAN), a wide area network (WAN), a global area network, or any number of private networks currently referred to as an Intranet, or any other network or combination of networks that can accommodate data communication. Such networks may be implemented with any number of hardware and/or software components, transmission media and/or network protocols. Although FIG. 1(a) illustrates the network 114 as a single network, the network 114 can include multiple interconnected networks.

Figure 1B:
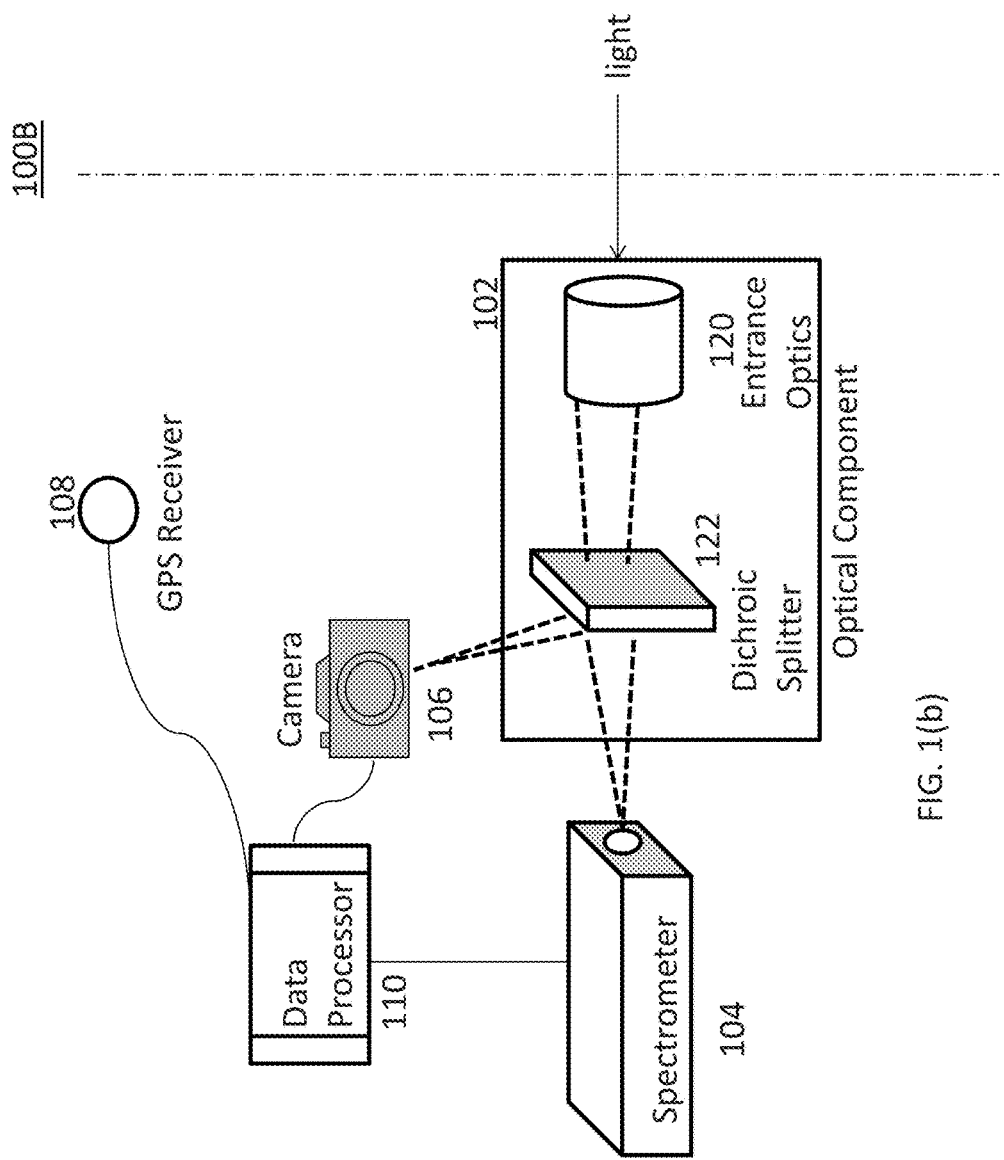

FIG. 1(b) illustrates an exemplary gas detector system 100B in accordance with an alternative embodiment of the disclosed subject matter. The system 100B comprises an optical component 102, a spectrometer 104, a camera 106, a GPS receiver 108, and a data processor 110. The components described in the system 100B can be further broken down into more than one component and/or combined together in any suitable arrangement. Further, one or more components can be rearranged, changed, added, and/or removed. For example, in some embodiments, the system 100B may also include a local storage medium and/or a remote storage medium.

In the system 100B, the optical component 102 collects and feeds the light to the spectrometer 104 and the camera 106. The receiver 108 receives location data from one or more satellites. The outputs of the spectrometer 104, the camera 106, and the GPS receiver 108 are sent to the data processor 110. In some embodiments, the optical component 102 further comprises two elements: an entrance optics 120 and a dichroic splitter 122. The components in the system 100B function essentially the same as the components described in the system 100A.

Figure 1C:
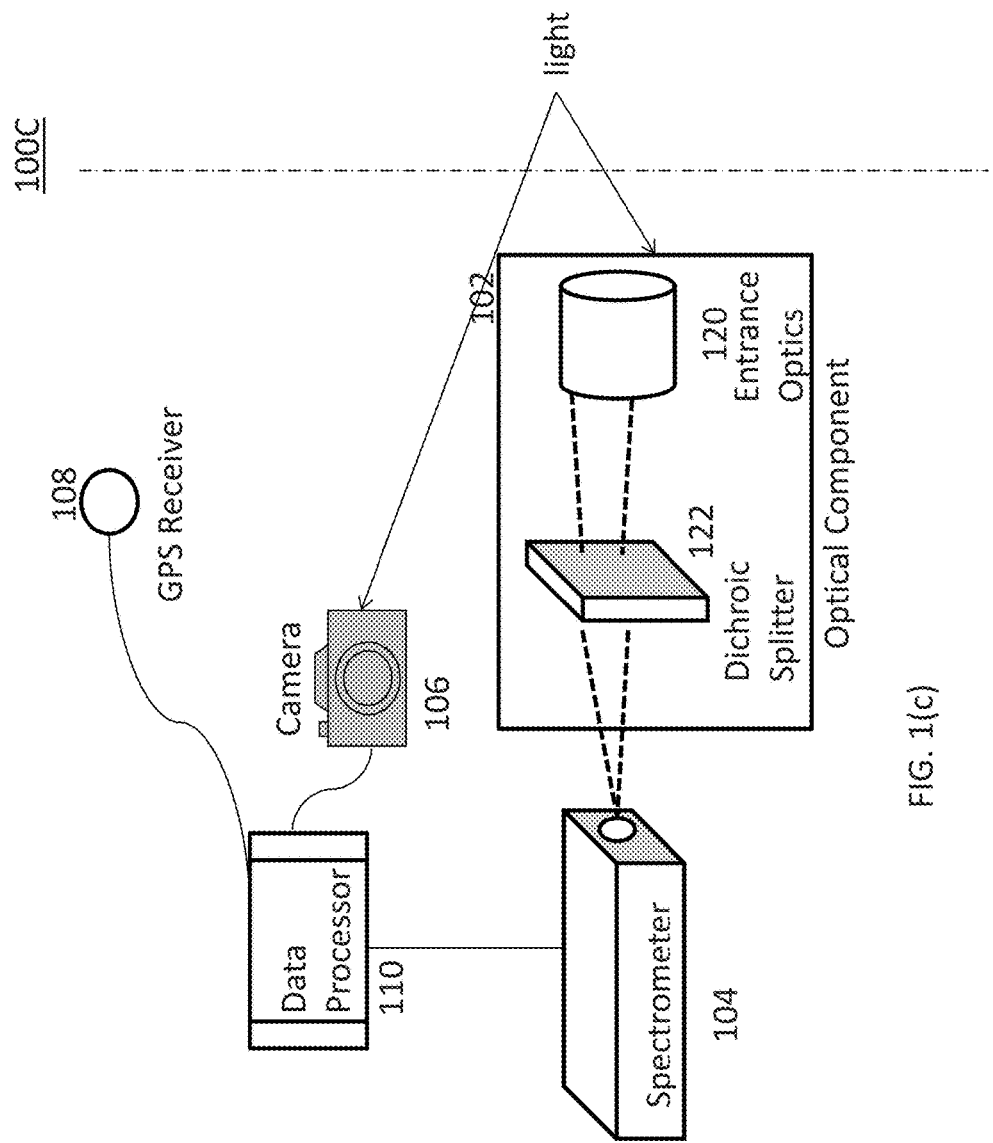

FIG. 1(c) illustrates an exemplary gas detector system 100C in accordance with an alternative embodiment of the disclosed subject matter. The system 100C comprises an optical component 102, a spectrometer 104, a camera 106, a GPS receiver 108, and a data processor 110. The components described in the system 100C can be further broken down into more than one component and/or combined together in any suitable arrangement. For example, the system 100C can also include the network 114 and/or the display 112 described in FIG. 1(a). Further, one or more components can be rearranged, changed, added, and/or removed. For example, in some embodiments, the system 100C may also include a local storage medium and/or a remote storage medium.

In the system 100C, the optical component 102 collects and feeds the light to the spectrometer 104. The camera 106 collects the light directly or from the optical component 102. The receiver 108 receives location data from one or more satellites. The outputs of the spectrometer 104, the camera 106, and the GPS receiver 108 are sent to the data processor 110. In some embodiments, the optical component 102 further comprises two elements: an entrance optics 120 and a dichroic splitter 122. The components in the system 100C function essentially the same as the components described in the systems 100A and/or 100B.

In the system 100C, the camera 106 can collect light directly with a built-in entrance optics. When the camera 106 and the spectrometer 104 do not use the exactly same entrance optics, the spectrometer 104 and the camera 106 can be co-registered with laboratory calibration to make sure that the camera 106 and the spectrometer 104 are pointing the same direction, so that the spectral data generated by the spectrometer 104 may be mapped to visible images generated by the camera 106 easily.

Figure 2:
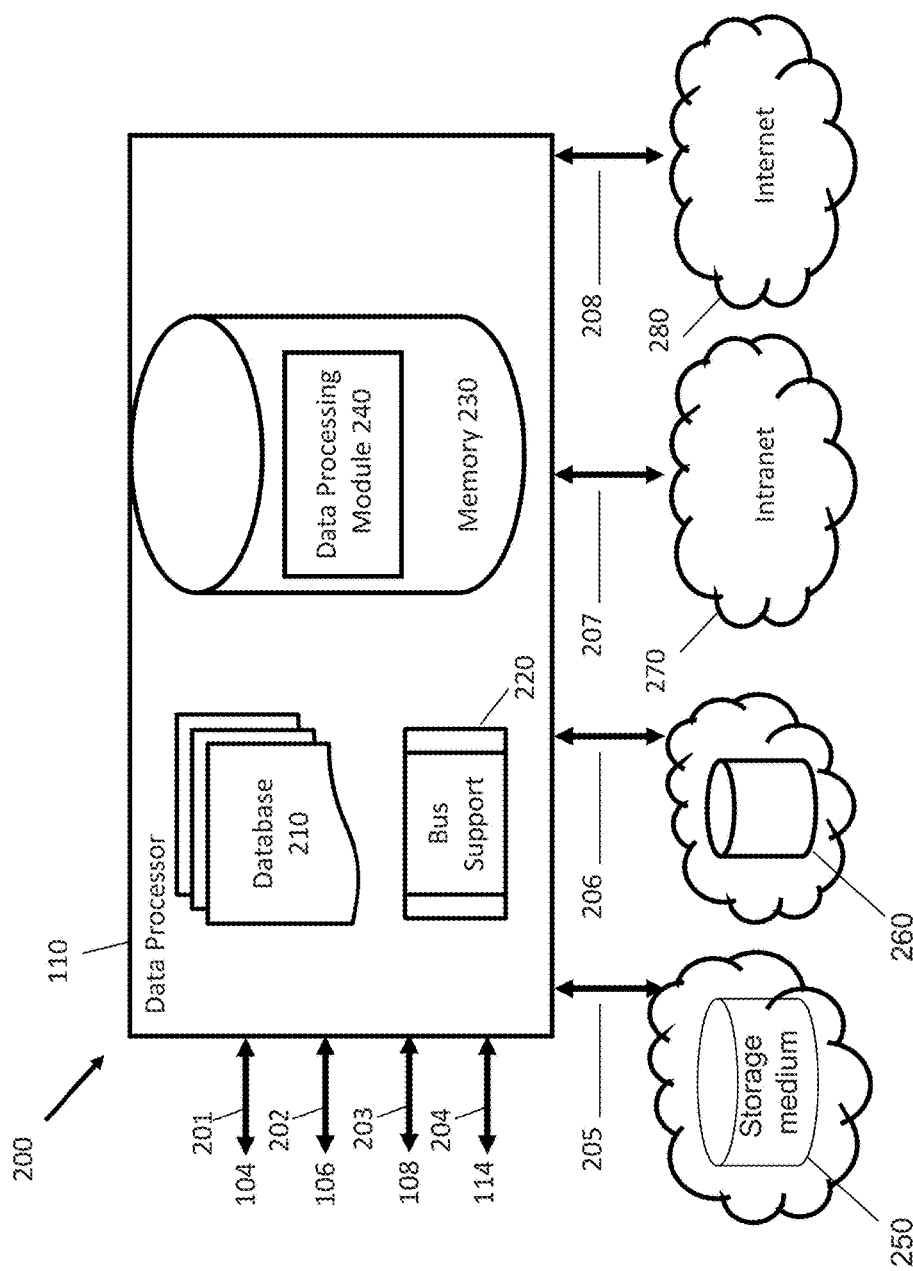
FIG. 2 illustrates a block diagram of a data processor in accordance with certain embodiments of the disclosed subject matter.

FIG. 2 is a block diagram of a data processor communicating with other components in accordance with certain embodiments of the disclosed subject matter. The block diagram 200 shows the data processor 110, interfaces 201-208, a local storage medium 250, a remote storage medium 260, an Intranet 270, and the Internet 280. The data processor 110 can communicate (1) with the spectrometer 104 (not shown) via the interface 201, (2) with the camera 106 (not shown) via the interface 202, (3) with the GPS receiver 108 (not shown) via the interface 203, (4) with the network 114 (not shown) via the interface 204, (5) with the local storage medium 250 via the interface 205, (6) with the remote storage medium 260 via the interface 206, (7) with the Intranet 270 via the interface 207, and (8) with the Internet 280 via the interface 208. The interfaces 201-208 are shown as separate interfaces but may be the same physical interface. The components described in the block diagram 200 can be further broken down into more than one component and/or combined together in any suitable arrangement. Further, one or more components can be rearranged, changed, added, and/or removed. In some embodiments, the data processor 110 can communicate with other components, such as the spectrometer 104, the camera 106, the GPS receiver 108, the local storage medium 250, the remote storage medium 260, the Intranet 270, and/or the Internet 280, directly or indirectly via the network 114.

The local storage medium 250 and the remote storage medium 260 can each include at least one physical, non-transitory storage medium, flash memory, a magnetic disk drive, an optical drive, a programmable read-only memory (PROM), a read-only memory (ROM), or any other memory or combination of memories. The local storage medium 250 and the remote storage medium 260 can be part of the data processor 110 or can be separated from the data processor 110.

The interfaces 201-208 provide an input and/or output mechanism to communicate with other components directly or indirectly over the network 114. The interfaces 201-208 can be implemented in hardware to send and receive signals in a variety of media, such as optical, copper, and wireless, and in a number of different protocols some of which may be non-transient.

The data processor 110 can be hardware that is configured to execute computer readable instructions such as software stored in temporary and/or permanent non-transitory memory. The data processor 110 can be a general processor or be an application specific hardware (e.g., an application specific integrated circuit (ASIC), programmable logic array (PLA), field programmable gate array (FPGA), or any other integrated circuit). The data processor 110 can execute computer instructions or computer code to perform desired tasks.

In some embodiments, the data processor 110 can operate using an operating system (OS) software. In some embodiments, the OS software is based on a Linux software kernel and runs specific applications in the server such as monitoring tasks and providing protocol stacks.

In some embodiments, the data processor 110 can reside in a data center and form a node in a cloud computing infrastructure. The data processor 110 can also provide services on demand. The data processor 110 on the cloud can be managed using a management system.

The data processor 110 comprises a database 210, a bus support 220, a memory 230, and a data processing module 240. The components described in the data processor 110 can be further broken down into more than one component and/or combined together in any suitable arrangement. Further, one or more components can be rearranged, changed, added, and/or removed. The database 210 and the data processing module 240 can be part of the memory 230 or can be separated from the memory 230.

The bus support 220 provides command and data handling for the components of the system 100. In some embodiments, the bus support 220 provides additional capabilities such as telemetry, attitude control, thermal control, power and power conditioning, structural support, orientation control, and/or other functionalities or combinations of functionalities that are typical on a satellite or instrument bus. The bus support 220 can be part of, or separate from, the data processor 110.

The database 210 can be configured to serve as a repository for all forms of data generated by the components of the system 100, including, without limitation, output data from the spectrometer 104, the camera 106, the GPS receiver 108, the display 112, the bus support 220, and/or the data processing module 240. The database 210 can be configured to provide data stored in the database 210 to other components of the system 100, including, without limitation, the display 112 and the data processing module 240. The database 210 can communicate with other components of the system 110 directly via one of the interfaces 201 to 208 or indirectly via the network 114. Furthermore, the database 210 can communicate with other components of the system 110 synchronously, asynchronously, or any suitable combination thereof. In some embodiments, the database 210 can also back up its data at the memory 230, the local storage medium 250, and/or the remote storage medium 260.

The data processing module 240 can be configured to process the raw spectral data generated by the spectrometer 104. Upon receiving the raw spectral data, the data processing module 240 can generate preprocessed spectral data by subtracting noise from the raw spectral data. The data processing module 240 can be configured to identify a first wavelength range that is sensitive to a target gas and a second wavelength range that is not sensitive to the target gas. After identifying the first and the second wavelength range, the data processing module 240 can be configured to process the preprocessed spectral data in the first wavelength range to generate an absorption power level and in the second wavelength range to generate a reference power level. The data processing module can then determine a concentration of the target gas by comparing the absorption power level to the reference power level. The data processing module 240 can also be configured to send any processed data to other components of the system 100, including, without limitation, the database 210 and the display 112.

In some embodiments, the data processing module 240 and the database 210 can be implemented in software using the memory 230. In some embodiments, the data from the database 210 and/or the data processing module 240 can be copied, moved, or backed up to the memory 230, the local storage medium 250, and/or the remote storage medium 260 from time to time or continuously, for archival or safety purposes. Although FIG. 2 shows the memory 230 as a single memory, the memory 230 can include more than one physical and/or logical memory. The memory 230 can be located in the same physical location as the data processor 110, at a remote location, or any other suitable location or combination of locations. The memory 230 can be a transitory or non-transitory computer readable medium, such as flash memory, a magnetic disk drive, an optical drive, a PROM, a ROM, or any other memory or combination of memories.

FIG. 2 shows the data processor 110 having data processing module 240 and database 210 that perform the above-described operations in accordance with certain embodiments of the disclosed subject matter. The data processor 110 may include additional modules, less modules, or any other suitable combination of modules that perform any suitable operation or combination of operations.

Figure 3:
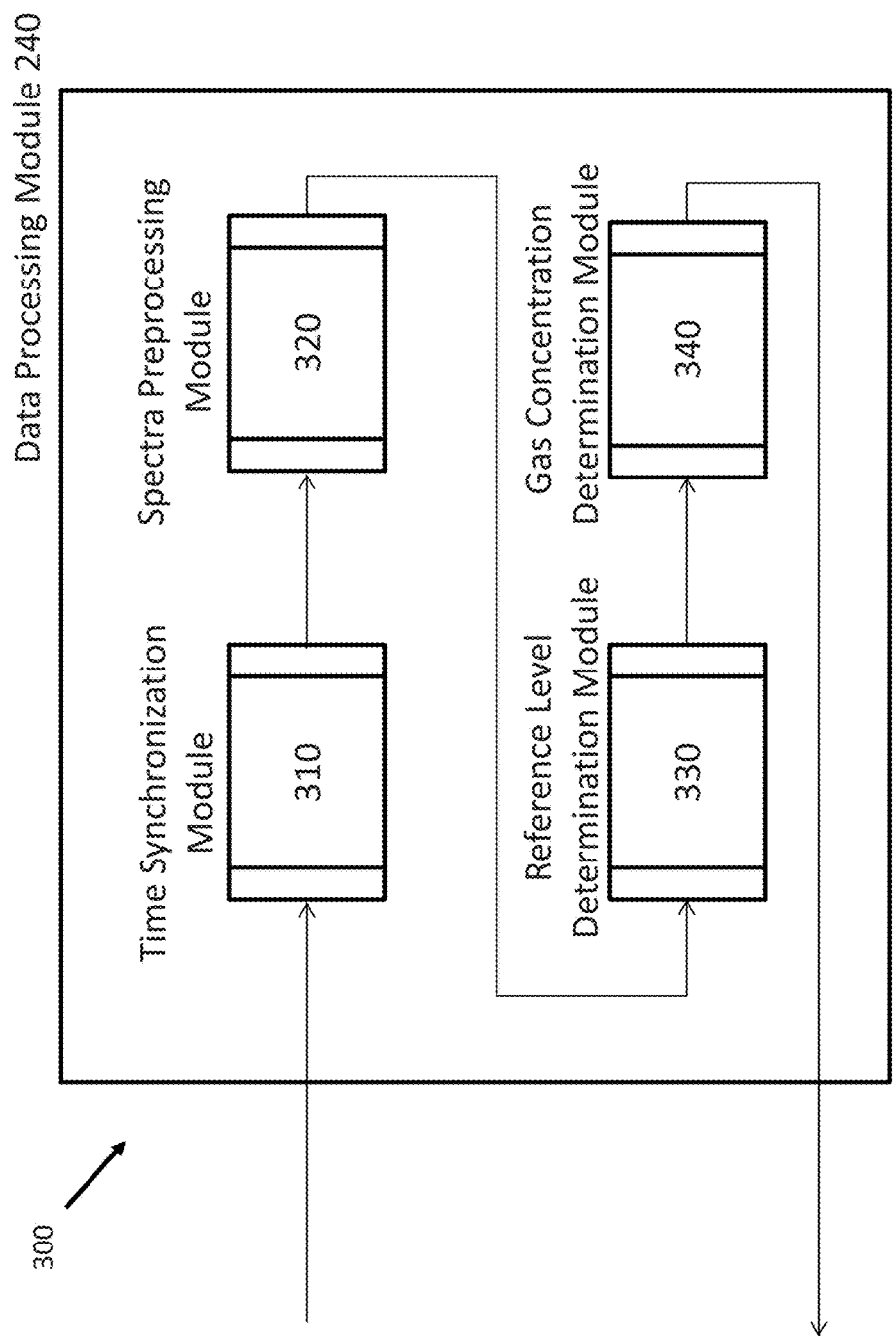
FIG. 3 illustrates a block diagram of a data processing module in accordance with certain embodiments of the disclosed subject matter.

FIG. 3 illustrates a block diagram of the data processing module 110 in accordance with certain embodiments of the disclosed subject matter. The data processing module 110 can further comprise four modules: a time synchronization module 310, a spectra preprocessing module 320, a reference level determination module 330, and a gas concentration determination module 340. Although the data processing module 240 is described as being made of four modules, these modules can be further broken down into more than one modules and/or combined together in any suitable arrangement. Further, one or more components can be rearranged, changed, added, and/or removed. For example, in some embodiments, the data processor 110 may not have the data processing module 240 as one level of hierarchy and directly have one or more of the four modules (e.g., the time synchronization module 310, the spectra preprocessing module 320, the reference level determination module 330, and the gas concentration determination module 340) interact with other components of the system 100. The structures, functions, and features of the time synchronization module 310, the spectra preprocessing module 320, the reference level determination module 330, and the gas concentration determination module 340 are described in more detail below with reference to FIG. 4.

Figure 4:
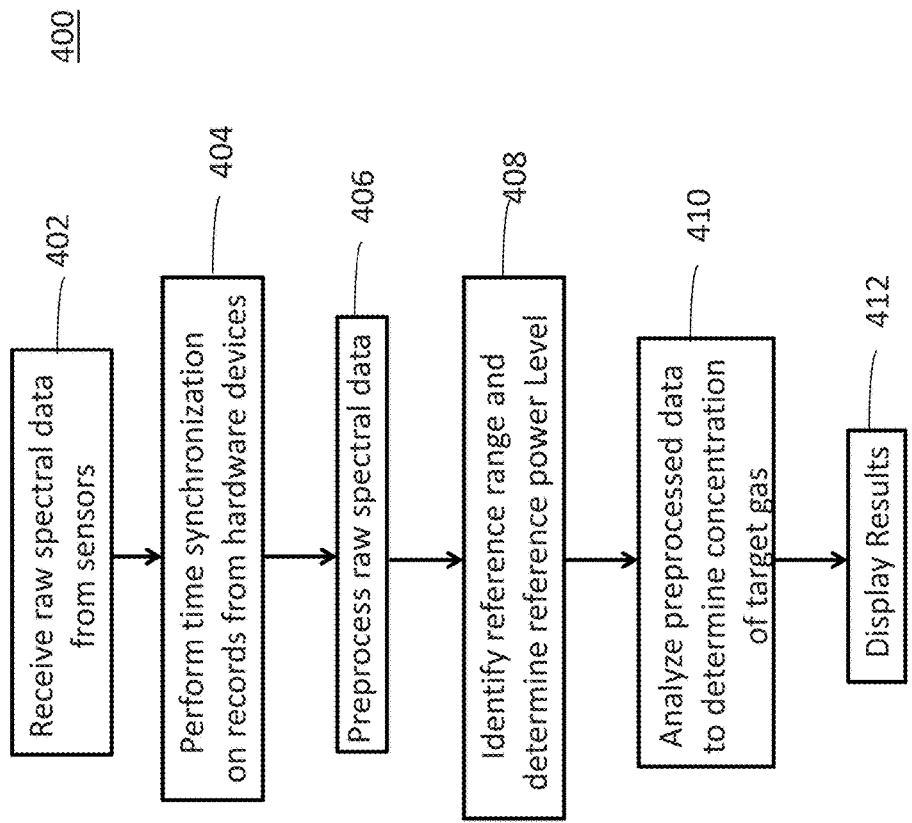
FIG. 4 illustrates a flow diagram illustrating the flow of data through the system in accordance with certain embodiments of the disclosed subject matter.

FIG. 4 illustrates a flow diagram illustrating a process 400 for processing data through the system in accordance with certain embodiments of the disclosed subject matter. The process 400 can be modified by, for example, having steps rearranged, changed, added, and/or removed. The process 400 may be performed after data collection is completed or in real-time/near-real-time while data acquisition continues.

At step 402, the data processor 110 receives raw data from the components of the system 100. The raw data can include, without limitation, one or more of the following data: the raw spectral data from the spectrometer 104, the time stamps and/or location stamps from the GPS receiver 108, and the images from the camera 106. After the raw data are received by the data processor, the raw data can be stored in the database 210 and processed by the data processing module 240. The process then proceeds to step 404.

At step 404, the digital processing module 240 can be configured to process the raw data received at step 402. In some embodiments, the time synchronization module 310 can be configured to tag or synchronize some or all raw data with mutually comparable timestamps. In some embodiments, time stamps can be master clock time stamps. For example, the time synchronization module 310 can be configured to synchronize the raw spectral data from the spectrometer 104 to determine the acquisition time in master clock, as the local CPU clock may have drifted over the time. In some embodiments, the synchronization with master clock time stamps can be performed by comparing the apparent clock time of the GPS receiver 108 at acquisition with an embedded GPS estimation of a master clock, thus allowing the translation from the apparent clock time of the GPS receiver to the master clock. In some embodiments, the images from the camera 106 can also be synchronized with master clock time stamps. The process 400 then proceeds to step 406.

At step 406, the synchronized raw spectral data from the time synchronization module 310 is then sent to the spectra preprocessing module 320, which performs preprocessing of the raw spectral data and determines absorption power level. Step 406 is described in more detail below with reference to FIG. 5. The process 400 then proceeds to step 408.

At step 408, the preprocessed spectral data from the spectra preprocessing module 320 is then sent to the reference level determination module 330. The reference level determination module 330 identifies a wavelength range that is not sensitive to the target gas and determines a corresponding reference power level over the reference range. As discussed earlier, the wavelength range that is not sensitive to the target gas is also referred to reference range. There are several reference ranges that are in proximity to the absorption lines of a particular target gas. Therefore, the intensity of light in the reference range represents a reference level to measure the intensity of light in the absorption lines. In some embodiments, the reference range can be determined in advance for the target gas. As an example, if the target gas is methane, then one of the reference ranges is approximately between 1.646527 micrometers and 1.647387 micrometers, which is in proximity to one absorption line of methane, approximately between 1.650823 micrometers and 1.651396 micrometers. Once the reference range is determined, power of the preprocessed spectral data around the reference range is used to establish the reference power level. This reference power level can be determined by averaging the power of the preprocessed spectral data across the reference range, by fitting some mathematical functions to the reference range, or by using the pixel-by-pixel data in the reference range as part of a comprehensive statistical analysis, such as a maximum likelihood analysis or other similar methods. In some embodiments, the reference power level can be the power of the preprocessed spectral data at one or more specific wavelengths within a reference range. In some embodiments, more than one reference range can be identified, and the reference power level can be calculated over the identified reference ranges. The reference power levels over a plurality of the reference ranges can be combined to provide a single reference power level, or kept separately for comparison to different absorption power levels at different absorption lines. The process 400 then proceeds to step 410.

At step 410, the absorption power level determined by the spectra preprocessing module 320 and the reference power level determined by the reference level determination module 330 are then sent to the gas concentration determination module 340. In the gas concentration determination module 340, the absorption power level is compared to the reference power level in a ratio. Creating this ratio serves to eliminate any irrelevant common mode effects that affect both the absorption power level and the reference power level. The common mode effects may include variations in pressure, temperature, presence of other gases not of interest, reflectivity of the reflecting surface, haziness or transmission of the atmosphere, solar illumination angle, and/or view angle, and any other effects that might change the overall brightness of the scene. The calculated ratio corresponds to the concentration of the target gas in the column of air among the system 100, the gas leak site, and the Sun. In some embodiments, the gas concentration determination module 340 can also determine other concentration metrics, including, without limitation, top leak sites and top leak periods.

Figure 6:
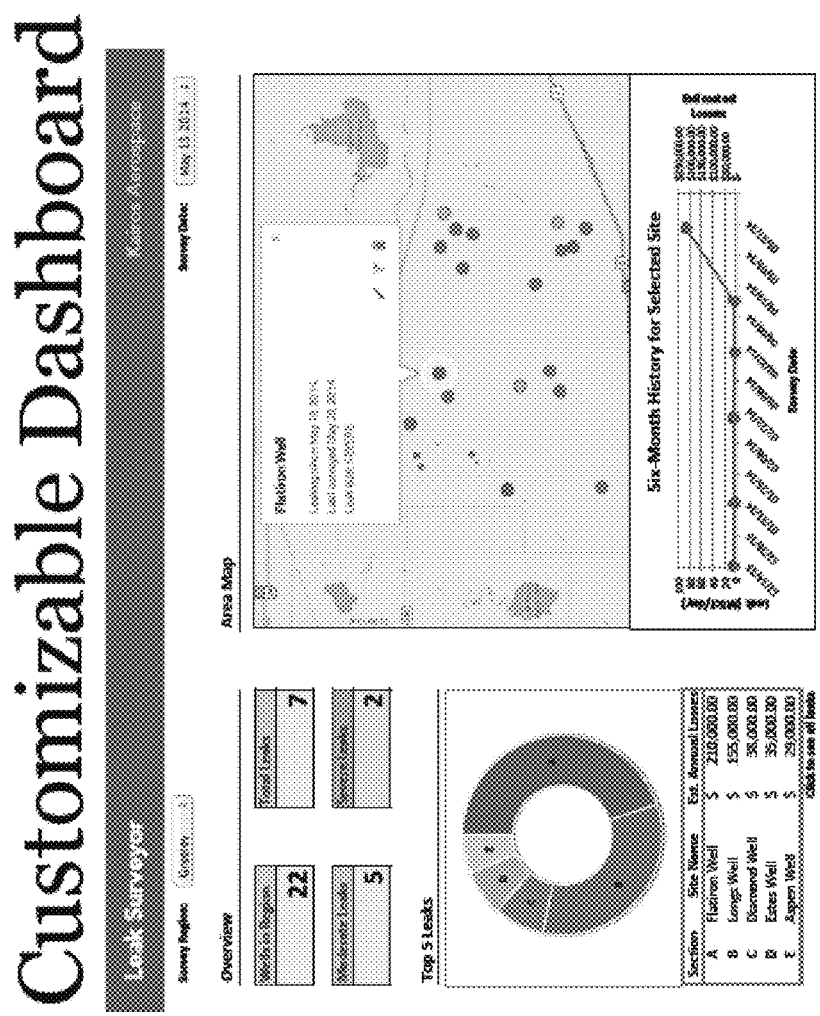
FIG. 6 illustrates an exemplary display of various results collected and processed by the gas detector system.

At step 412, one or more outputs generated by the components of the system 100 can be displayed by the display 112. For example, the display 112 can display, without limitation, one or more of the following data: the output from the optical component 102, the raw spectral data, the preprocessed spectral data, the absorption lines, the absorption power level, the reference range, the reference power level, the concentration ratio, other concentration metrics, and the images generated by the camera 106. FIG. 6 illustrates an exemplary display of various results collected and processed by the system 100. One or more contents can be rearranged, changed, added, and/or removed based on requirements of the customers and regulators.

Although in the previous paragraphs, the steps 404, 406, 408, and 410 are respectively processed by the time synchronization module 310, the spectra preprocessing module 320, the reference level determination module 330, and the gas concentration determination module 340, in some embodiments these steps can be equally handled by the data processing module 240, other modules of the data processing module 240, other modules of the data processor 110, or any suitable combinations thereof. Any data generated in the process 400 can be stored in the database 210, the memory 230, the local storage medium 250, the remote storage medium 260, and/or other components of the system 100 for future analysis.

Figure 5:
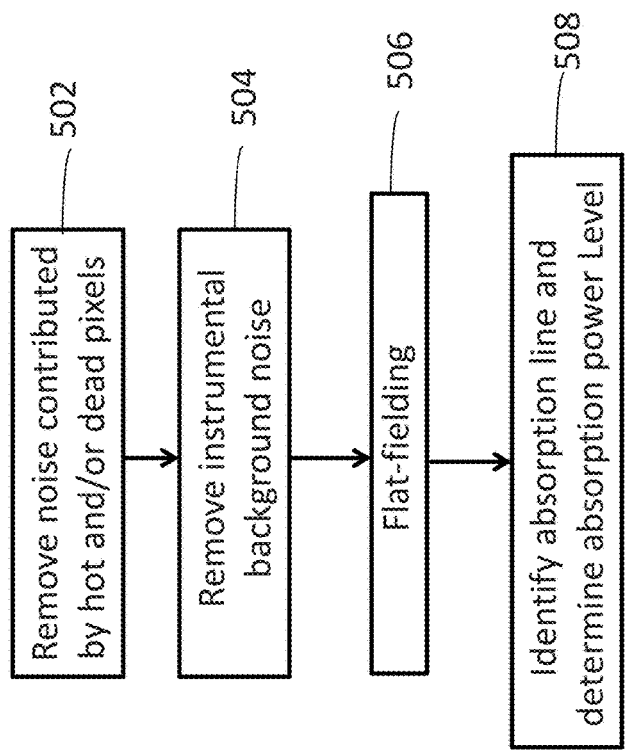
FIG. 5 illustrates a flow diagram illustrating the flow of preprocessing spectral data in accordance with certain embodiments of the disclosed subject matter.

FIG. 5 illustrates a flow diagram illustrating step 406 for preprocessing the raw spectral data in accordance with certain embodiments of the disclosed subject matter. The steps illustrated in FIG. 5 can be modified by, for example, having steps rearranged, changed, added, and/or removed.

At step 502, the spectra preprocessing module 320 removes noise caused by hot and/or dead pixels of the spectrometer 104. The raw spectral data from the spectrometer generally consist of pixel count data in a one-dimensional (for a standard spectrometer) or two-dimensional (for an imaging spectrometer) matrix array. Hot or dead pixels may artificially increase or decrease the pixel count data. The information of the hot or dead pixels can be obtained from a predetermined list or through calibration.

At step 504, the spectra preprocessing module 320 removes instrumental background noise. Generally, the instrumental background noise of a sensor device, such as the optical component 102 and the spectrometer 104, exhibits two types of noise: the read noise and the dark current noise. Read noise manifests as a fixed number of counts in each pixel that arises from the process of reading out the pixel. Typically, read noise in a given pixel can be measured, and each read operation produces a number of read noise counts drawn from a Poisson distribution about a stable expected value. Dark current noise arises from electrons that drift into the pixel. Therefore, the expected number of dark current counts in a pixel is proportional to the exposure time, and the actual number is drawn from a Poisson distribution about that expected number. Various methods are common for the subtraction of the read noise and the dark current noise. In some embodiments, the sum of the expected value of the read noise and the dark current noise is subtracted from the raw spectral data in each pixel. This expected noise value can be assumed the same for each pixel, or may be measured under test circumstances on a pixel-by-pixel basis. The expected noise value may be stored in the database 210, the memory 230, the local storage medium 250, the remote storage medium 260, and/or other components of the system 100. In some embodiments, user may externally supply the expected noise value to the spectra preprocessing module 320.

At step 506, the raw spectral data may be further processed in the spectral preprocessing module 320 by a process of flat-fielding, where variations in gain in different detector pixels are compensated by adjusting the raw spectral data depending on the previously-measured gain in each pixel. The pixel-dependent gain values may be acquired from the manufacturer, from direct calibration measurement of a known uniform source, or from other means. The pixel-dependent gain values may be saved in the database 210, the memory 230, the local storage medium 250, the remote storage medium 260, and/or other components of the system 100. In some embodiments, the pixel-dependent gain values may be saved as some functional forms, such as uniform, linear, or some higher order, or other functional shapes across the raw spectral data. In some embodiments, the pixel-dependent gain values may be saved as individual gain values on a pixel-by-pixel basis. The raw spectral data are converted to preprocessed spectral data after step 506.

At step 508, the spectral preprocessing module 320 can be configured to identify a wavelength range that is sensitive to the target gas and calculate a corresponding absorption power level around the identified wavelength range. As discussed earlier, the wavelength range that is sensitive to the target gas is also referred to absorption line. The absorption lines for different target gases are publicly available through database such as the HITRAN database. Once the absorption line for the target case is identified, the absorption power level can be determined by finding power of the preprocessed spectral data around the identified absorption line of the target gas. As an example, if the target gas is methane, then one absorption line is known to be approximately between 1.650823 micrometers and 1.651396 micrometers. The corresponding absorption power level is the power of the preprocessed spectral data approximately between 1.650823 micrometers and 1.651396 micrometers. In some embodiments, the corresponding absorption power level can be the power of the preprocessed spectral data at one or more specific wavelengths within an absorption line. The power of preprocessed spectral data can be calculated by using a statistical fitting with generic line shapes, one- or two-parameter Gaussian shapes, or line shapes actually measured for the spectrometer 104. The statistical fitting could be a simple chi-squared minimization, a maximum likelihood estimate, or a Bayesian estimate. It will be apparent to those skilled in the art that a variety of well-known statistical fitting techniques could be employed to estimate the absorption power level. In some embodiments, more than one absorption line can be identified, and the absorption power level can be calculated over the identified absorption lines. The absorption power levels over a plurality of the reference ranges can be combined to provide a single absorption power level, or kept separately for comparison to different reference power levels at different reference ranges. In some embodiments, knowledge of the relative strength of various absorption lines recorded in publicly available databases such as HITRAN can be used to create a single absorption curve comprising multiple lines. This curve can then be scaled, with the scaling parameter affecting some or all of the absorption lines simultaneously, and with the scaling parameter determined by a suitable means of fitting to the data, in order to minimize the effect of Poisson noise in the data on the eventual estimate of the scaling parameter.

Figure 7:
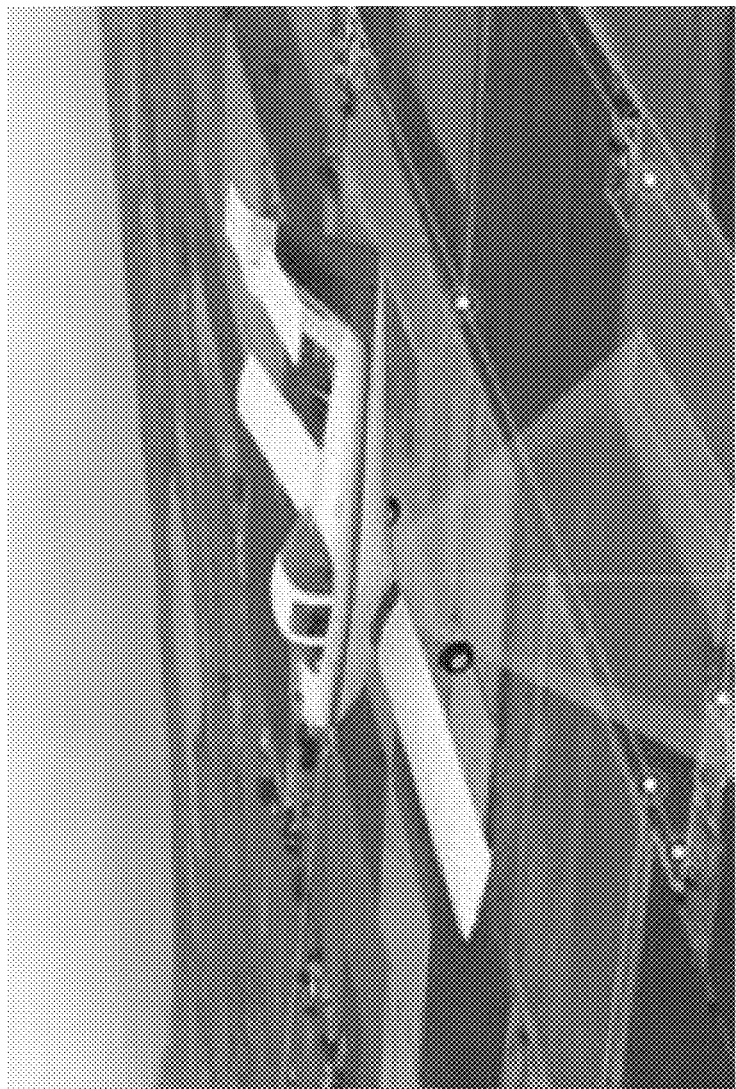
FIG. 7 illustrates an exemplar embodiment where the gas detector system is mounted on an airplane.
Figure 8:
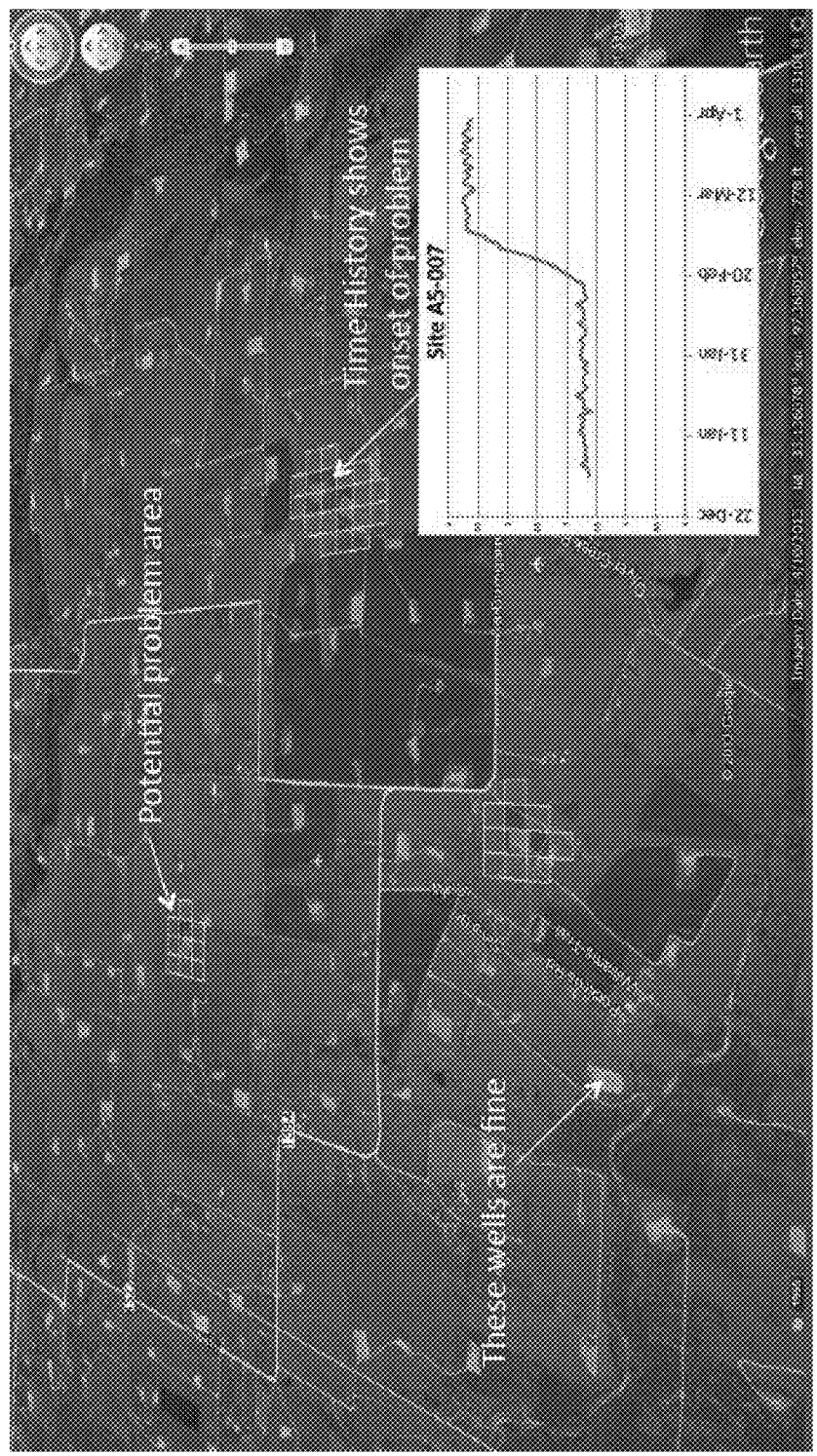
FIG. 8 illustrates a natural gas field with indications of potential gas leak area.

The systems 100 can be instantiated in several related ways. In some embodiments, the systems 100 may be mounted on any suitable elevated location, including fixed stands or buildings, balloons, aerostats, or other lighter-than-air vehicles, kites, unmanned aerial vehicles, airplanes, helicopters, or other devices. For example, FIG. 7 illustrates an embodiment, where the system is mounted on an airplane. In some embodiments, the system 100C is compact enough to be pointed at an area of interest. In operation, the optical component 102 is oriented downwards towards the ground such that the sunlight reflecting off the ground passes through the gas of interest, and the absorption of the sunlight in the absorption wavelength is measured. In some embodiments, a suitably bright artificial light source could be used in place of the sun. In some embodiments, the optical component 102 could, with suitable filters in place, be pointed directly at the sun from the ground through the target gas, rather than using reflected sunlight. FIG. 8 illustrates an exemplary image of gas leak site viewed by the systems 100 mounted on an airplane.

In some embodiments, the system may be implemented on a satellite or constellation of satellites, each containing substantially similar systems or improvements thereupon. In some embodiments, these satellites would orbit the Earth in a polar orbit, designed to provide coverage to every point on the Earth at daily, weekly, or other frequencies. The push broom would extend in the cross-track direction, and the width of the broom is adjustable. In one embodiment, the width of the broom can be approximately 200 kilometers. In some embodiments, larger or smaller width can also be provided. This embodiment would have the advantage of frequent, worldwide coverage in leak detection. The scaling effect would lead to a cost-effective way of monitoring sites. This way of monitoring is unaffected by terrain or difficulty of access and allows to cover large areas quickly and efficiently. FIG. 9 illustrates the concept that the system 100 can be implemented on one or more satellites.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

What is claimed is:

1. An apparatus for detecting gas leaks, comprising:
   an entrance optic configured to collect light from a region;
   a camera providing an image of at least a part of the region using at least a portion of the collected light;
   a spectrometer configured to receive and process the light to generate raw spectral data, wherein the camera and the spectrometer lack therebetween electrical communication by an electrical conductor or wirelessly for synchronization;
   a memory that stores instructions; and
   a processor configured to run the instructions, causing the processor to:
   receive the raw spectral data,
   generate preprocessed spectral data by subtracting noise from the raw spectral data,
   identify a first wavelength range that is sensitive to a target gas and a second wavelength range that is not sensitive to the target gas,
   process the preprocessed spectral data in the first wavelength range to generate an absorption power level,
   process the preprocessed spectral data in the second wavelength range to generate a reference power level,
   compare the absorption power level to the reference power level to determine a concentration of the target gas; and
   map the concentration of the target gas to the image using a timestamp that provides synchronization between the raw spectral data and the image.

2. The apparatus of claim 1, further comprising an optical component comprising:
   the entrance optic; and
   a dichroic splitter configured to split the collected light into at least a first portion of the light and a second portion of the light.

3. The apparatus of claim 2, wherein the collected light comprises visible light reflected from the region.

4. The apparatus of claim 2, wherein the spectrometer is configured to receive and process the second portion of the light to generate the raw spectral data.

5. The apparatus of claim 2, wherein the first portion of the light is visible light and the second portion of the light is infrared light.

6. The apparatus of claim 1, wherein the spectrometer is a hyperspectral imaging spectrometer.

7. The apparatus of claim 1, wherein the spectrometer further comprises an InGaAs detector.

8. The apparatus of claim 1, further comprising:
   a GPS receiver configured to record at least one of the following:

a location stamp associated with when the entrance optic collected the light, and a time stamp associated with when the entrance optic collected the light, wherein the running of the instructions further causes the processor to match the raw spectral data with at least one of the location stamp and the time stamp.

9. The apparatus of claim 1, further comprising a display unit configured to display at least one of the following:

a first output from an optical component comprising the entrance optic;

a second output from the spectrometer comprising the raw spectral data;

a third output from the processor comprising the preprocessed spectral data; and a fourth output from the processor comprising the concentration of the target gas.

10. The apparatus of claim 1, wherein the target gas is methane and the first wavelength range is around 1.65 micrometers.

11. A method for detecting gas leaks, comprising:

collecting light from a region;

processing the light to generate an image of at least a part of the region and raw spectral data, the generation of the image being electrically independent of the generation of the raw spectral data;

generating preprocessed spectral data by subtracting noise from the raw spectral data;

identifying a first wavelength range that is sensitive to a target gas and a second wavelength range that is not sensitive to the target gas;

processing the preprocessed spectral data in the first wavelength range to generate an absorption power level;

processing the preprocessed spectral data in the second wavelength range to generate a reference power level;

comparing the absorption power level to the reference power level to determine a concentration of the target gas; and mapping the concentration of the target gas to the image using a timestamp that provides synchronization between the raw spectral data and the image.

12. The method of claim 11, further comprising splitting the light into at least a first portion of the light and a second portion of the light, wherein the image is generated from the first portion of the light.

13. The method of claim 11, wherein the light comprises visible light reflected from the region.

14. The method of claim 12, wherein processing the light to generate the raw spectral data comprises processing the second portion of the light to generate the raw spectral data.

15. The method of claim 12, wherein the first portion of the light is visible light and the second portion of the light is infrared light.

16. The method of claim 11, further comprising:

recording at least one of the following:

a location stamp associated with when the light is collected, and a time stamp associated with when the light is collected; and matching the raw spectral data with at least one of the location stamp and the time stamp.

17. The method of claim 11, further comprising displaying at least one of the following:

a first output comprising the light;

a second output comprising the raw spectral data;

a third output comprising the preprocessed spectral data; or a fourth output comprising the concentration of the target gas.

18. The method of claim 11, further comprising identifying the first wavelength range to be around 1.65 micrometers to detect the target gas as methane.

19. A non-transitory computer readable medium having executable instructions operable to cause an apparatus to:

collect light from a region;

process the light to generate an image of at least a part of the region and raw spectral data, the generation of the image being electrically independent of the generation of the raw spectral data;

generate preprocessed spectral data by subtracting noise from the raw spectral data;

identify a first wavelength range that is sensitive to a target gas and a second wavelength range that is not sensitive to the target gas;

process the preprocessed spectral data in the first wavelength range to generate an absorption power level;

process the preprocessed spectral data in the second wavelength range to generate a reference power level;

compare the absorption power level to the reference power level to determine a concentration of the target gas; and map the concentration of the target gas to the image using a timestamp that provides synchronization between the raw spectral data and the image.

20. The computer readable medium of claim 19, wherein the executable instructions are further operable to cause the apparatus to record at least one of the following:

a location stamp associated with when the light is collected; and a time stamp associated with when the light is collected.

* * * * *